Nov. 8, 1949. H. C. SWIM Plant Pat. 894
ROSE PLANT
Filed March 23, 1948
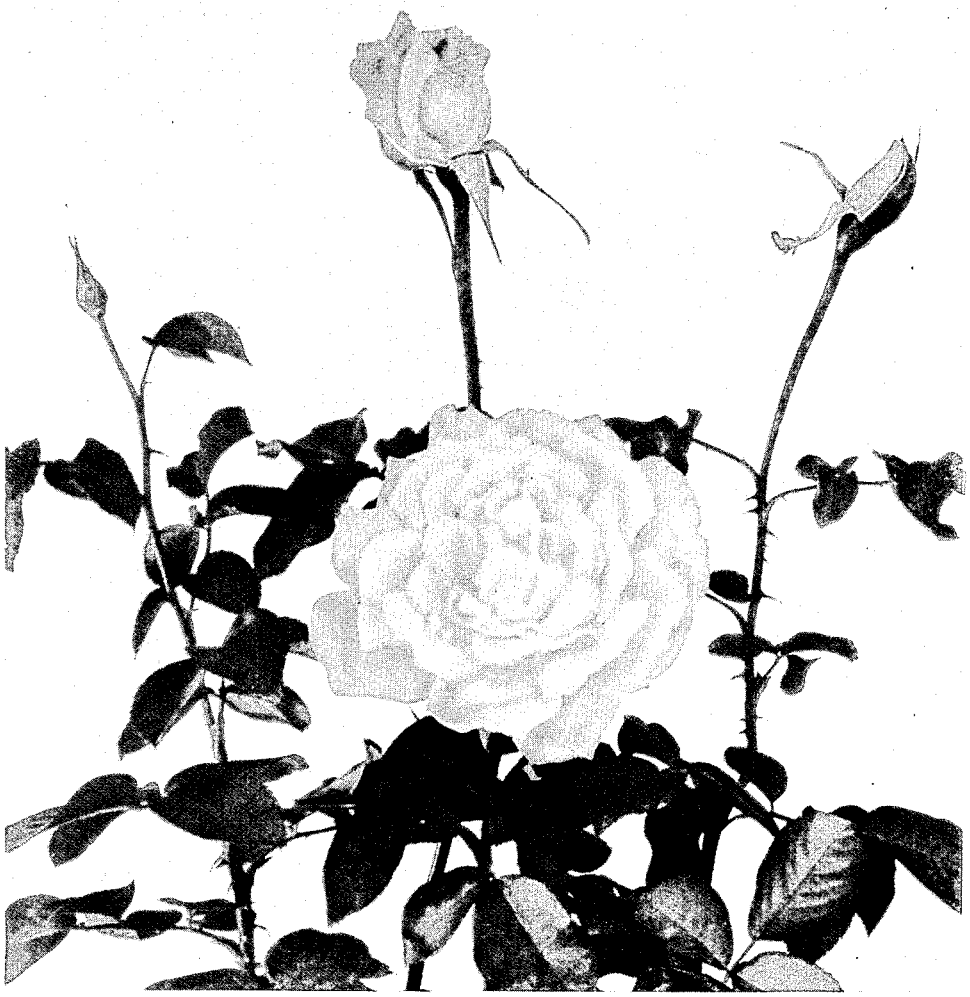
Inventor
H. C. Swim
By Robb & Robb
Attorneys Patented Nov. 8, 1949

Plant Pat. 894

UNITED STATES PATENT OFFICE

894

ROSE PLANT

Herbert C. Swim, Ontario, Calif., assignor to Armstrong Nurseries, Inc., Ontario, Calif., a corporation of California Application March 23, 1948, Serial No. 16,589

1 Claim. (Cl. 47—61)

The present invention relates to a new and distinct variety of hybrid tea rose plant especially useful for cut flower and garden decoration.

This new variety is a free-branching, floriferous plant, abundantly clothed with medium to large, heavy, leathery, glossy foliage, a combination giving the plant an attractive appearance for use in garden decoration.

Further important characteristics relating particularly to its field of utility reside in its semi-double flower with 17 to 21 petals, in a color, which so far as I am aware, is new in roses, but one which is difficult to describe any more closely than is specifically set forth hereinafter, and the habit of usually flowering in clusters but with the stems of the individual flowers relatively long, so that the flowers may be cut individually, if desired.

This clustering flower characteristic, combined with the free production of such clusters, gives the plants of this new variety a free or mass display of blooms in the garden somewhat comparable to plants of varieties in the floribunda class but with individual flowers larger than is characteristic of this latter group.

This new variety differs from its pollen parent in the following characteristics:

(1) This new variety is much more vigorous, floriferous, and abundant in foliage than its pollen parent.

(2) The color of the flower is very much more brilliant than is characteristic of the pollen parent.

(3) Petalage of this new variety classes it as a semi-double, whereas petalage of the pollen plant would place it in the class of double roses.

The present variety also differs from its seed parent in the following respects:

(1) This new variety is characterized by glossy foliage whereas "Charlotte Armstrong" is characterized by foliage generally classified as dull-surfaced.

(2) This new variety produces the majority of its flowers in clusters whereas "Charlotte Armstrong" produces them with a single flower to a stem.

(3) This new variety has an entirely different color of flower than "Charlotte Armstrong" as well as being distinct from it in shape of bud.

(4) This new variety has no small prickles whereas "Charlotte Armstrong" has many.

(5) This new variety is bushy and compact whereas "Charlotte Armstrong" is tall and rangy.

Asexual reproduction shows that the characteristics hold true through succeeding propagations.

In the drawings are illustrated specimens of the flowers at different stages of development and the young and mature foliage.

The following is a detailed description of the new variety, all reference to color being an accordance with the Robert F. Wilson's Horticultural Colour Chart, except where indicated to be in accordance with Ridgway's Color Standards and Nomenclature:

Type: Hardiness untested; bush; outdoor; seedling; for cut flowers and garden decoration.

Class: Hybrid tea.

Breeding: Seedling.

*Seed parent.*—"Charlotte Armstrong," Plant Patent No. 455.

*Pollen parent.*—Unnamed seedling.

Propagation: Holds its distinguishing characteristics through succeeding propagations by budding, the only method tried so far.

*Flower*

Locality where grown: Ontario, California.

Flowers borne: Sometimes singly, usually three to four and occasionally more to stem; in irregular cluster; on normal strength, medium length stems.

Quantity of bloom: Abundant; outdoors.

Continuity: Intermittent during growing season.

Fragerance: Moderate; spicy.

Bud:

*Peduncle.*—Medium to long; moderately heavy; erect to stiff; moderately rough; numerous gland-tipped cilia and prickles. *Color*—near Deep Chrysolite Green, Plate XXXI (Ridgway), becoming washed with Morocco Red, Plate I (Ridgway) on side exposed to sun late in season.

*Before calyx breaks.*—*Size*—medium. *Form*—long; pointed; with foliaceous appendages, tomentum, gland-tipped cilia on the surface of the bud; with slender, much cut foliaceous parts extending beyond the tip of the bud equal to ¾ or more of its length.

*As calyx breaks.*—Color—near Cardinal Red, Plate 822, page 168. *Sepals*—inner surface—with fine, wooly tomentum. Margins covered by adjacent sepals have fine woolly tomentum, but margins not covered by adjacent sepals have fine wooly tomentum and stipitate glands.

*As first petal opens.*—*Size*—medium. *Form*—long; pointed. *Color*—outside: Turkey Red, Plate 721/2, page 94, with a spot of Aureolin, Plate 3/1, page 3, at base of petal; inside: Turkey Red, Plate 721, page 94, with a large spot of Aureolin, Plate 3, page 3, at base of petal.

*Opening.*—Opens up well.

Bloom: Size, when fully open—medium to large; 3½" to 4½".

*Petalage.*—Semi-double; from 17 to 21 petals; arranged irregularly; usually 3 to 5 petaloids arranged irregularly.

*Form.*—Open; high center at first; becoming flat; petals remaining at first very loosely rolled outward; becoming later, at maturity, loosely rolled outward on lateral margins.

Petals: Thick; with inside velvety and outside satiny.

*Shape.*—Outside—obovate; scalloped with one to two notches. Intermediate—obovate; scalloped with one to two notches. Inside—obovate; scalloped irregular with one to two notches.

*Color.*—Colors may be modified by being striped, shaded, washed with other colors.

This description of a newly opened flower was made from a rose grown outdoors in the month of November, at Ontario, California:

*Color.*—*Outside petal*—outside surface: near Cherry, Plate 722/2, page 157, with a spot of Aureolin, Plate 3/1, page 3, at base of petal; inside surface: near Cherry, Plate 722, page 157, with large spot of Aureolin, Plate 3, page 3, at base of petal. *Intermediate petal*—outside surface: near Cherry, Plate 722/2, page 157, with a spot of Aureolin, Plate 3/1, page 3, at base of petal, occasionally with a streak of Aureolin, Plate 3/3, page 3, from base of petal to apex; inside surface: near Cherry, Plate 722, page 157, with a spot of Aureolin, Plate 3, page 3, at base of petal. *Inner petal*—outside surface: near Cherry, Plate 722/2, page 157, with a spot of Aureolin, Plate 3/1, page 3, at base of petal, occasionally with a streak of Aureolin, Plate 3/3, page 3, from base of petal to apex; inside surface: near Cherry, Plate 722, page 157, becoming washed near base of petal with Signal Red, Plate 719/1, page 93, with a spot of Aureolin, Plate 3, page 3, at base of petal.

This description was made from a rose that was open for three days indoors in the month of November, at Ontario, California:

*Color.*—*Outside petal*—outside surface: near Neyron Rose, Plate 623, page 76, with a spot of Aureolin, Plate 3/1, page 3, at base of petal; inside surface: near Rose Madder, Plate 23, page 23, with a large spot of Aureolin, Plate 3/1, page 3, at base of petal. *Inside petal*—outside surface: near Neyron Rose, Plate 623/1, page 76, with a spot of Aureolin, Plate 3/1, page 3, at base of petal, occasionally with a streak of Aureolin, Plate 3/2, page 3, from base of petal to near apex of petal; inside surface: near Rose Madder, Plate 23/1, page 23, with a spot of Aureolin, Plate 3/1, page 3, at base of petal.

*General color effect.*—Newly opened flower—near Cherry, Plate 722, page 157. Three days open—near Rose Madder, Plate 23/1, page 23.

*Behavior.*—Drop off cleanly; fading lighter, becoming only slightly purple; affected by hot, dry weather, fading to a lighter shade of red with the number of petals reduced materially.

*Flower longevity.*—On bush in garden—3 to 4 days in November. Cut roses grown outdoors kept at living-room temperatures—2 to 3 days in November.

*Reproductive organs*

Stamens: Many, about 90 in number; arranged regularly about pistils.

Filaments: Long, from 5–14 mm. in length. *Color*—Poppy Red, Plate 16/1, page 16, shading to Tangerine Orange, Plate 9/2, page 9, near apex; most with anthers.

Anthers: Medium to large; all open at once. *Color*—near Saffron Yellow, Plate 7/2, page 7.

Pollen: Abundant. *Color*—near Cadmium Orange, Plate 8/1, page 8.

Pistils: Medium to many; about 50 in number.

Styles: Uneven; medium to long; 5 to 12 mm. in length; loosely bunched; medium caliper. *Color*—Sap Green, Plate 62/3, page 62, at base, becoming Currant Red, Plate 821, page 167, at apex.

Stigma: Translucent but near Aureolin, Plate 3/3, page 3.

Ovaries: Some protruding from calyx.

Hips: Globular; very smooth; walls thick, semi-dry. *Color*—from Olive-Yellow, Plate XXX (Ridgway), to Honey Yellow, Plate XXX (Ridgway).

Sepals: Falling soon; moderately long; curled. *Color*—inside: near Tawny-Olive, Plate XXIX (Ridgway); outside: near Tawny-Olive, Plate XXIX (Ridgway).

Seeds: Few to many, usually from 4 to 14 in number; medium size.

Foliage:

*Leaves.*—Compound of five to seven leaflets; abundant; medium to large; heavy; leathery; glossy.

*Leaflets.*—Shape—ovate lanceolate, with apex acute. Base-round. Margin—simply, sometimes doubly, serrate.

*Color.*—*Mature*—upper surface: near Yew Green, Plate XXXI (Ridgway); under surface: near Asphodel Green, Plate XLI (Ridgway), washed with near Dark Indian Red, Plate XXVII (Ridgway). *Young*—upper surface: near Light Cress Green, Plate XXXI (Ridgway); under surface: near Absinthe Green, Plate XXXI (Ridgway), washed with Vandyke Red, Plate XIII (Ridgway).

*Rachis.*—Medium to heavy. Upper side—grooved; glandular. Under side—prickly.

*Stipules.*—Moderately long; moderately wide; with short points turning out at an angle of less than 45°.

*Disease.*—Moderately resistant to mildew.

Growth:

*Habit.*—bushy; upright; much branched.

*Growth.*—Free to vigorous.

*Canes.*—Moderately heavy.

*Main stems.*—Color—near Light Cress Green, Plate XXXI (Ridgway). *Large prickles*—many; long; slightly hooked downward; with long narrow base. Color—near Russet, Plate XV (Ridgway). *Small prickles*—none. *Hairs*—none.

*Branches.*—Color—near Rainette Green, Plate XXXI (Ridgway). *Large prickles*—several to many; medium length; slightly hooked downward; with long narrow base. Color—near Garnet Brown, Plate I (Ridgway). *Small prickles*—none. *Hairs*—none.

*New shoots.*—Color—near Absinthe Green, Plate XXI (Ridgway), washed with near Vandyke Red, Plate XIII (Ridgway). *Large prickles*—several to many; long; slightly hooked downward: with long narrow base. Color—near Vandyke Red, Plate XIII (Ridgway). *Small prickles*—none. *Hairs*—none.

I claim:

A new and distinct variety of rose plant characterized as to novelty by its free branching and floriferousness; its abundant medium to large, heavy, leathery and glossy foliage; its semi-double flower with an average of seventeen to twenty-one petals of unique and brilliant color; and its habit of flowering in clusters but on relatively long individual stems adapting it to cut flower purposes and garden decoration, substantially as shown and described.

HERBERT C. SWIM.

No references cited.